(12) United States Patent
Döring

(10) Patent No.: US 9,079,932 B2
(45) Date of Patent: Jul. 14, 2015

(54) METHOD FOR INCREASING THE YIELD IN LACTOSE PRODUCTION (III)

(71) Applicant: DMK Deutsches Milchkontor GmbH, Zeven (DE)

(72) Inventor: Sven-Rainer Döring, Zeven (DE)

(73) Assignee: DMK Deutsches Milchkontor GmbH, Zeven (DE)

( * ) Notice: Subject to any disclaimer, the term of this patent is extended or adjusted under 35 U.S.C. 154(b) by 2 days.

(21) Appl. No.: 14/177,837

(22) Filed: Feb. 11, 2014

(65) Prior Publication Data

US 2014/0235849 A1 Aug. 21, 2014

(30) Foreign Application Priority Data

Feb. 16, 2013 (EP) .................................... 13155557

(51) Int. Cl.
    *C07H 3/04* (2006.01)
    *C13K 5/00* (2006.01)

(52) U.S. Cl.
    CPC ... *C07H 3/04* (2013.01); *C13K 5/00* (2013.01)

(58) Field of Classification Search
    None
    See application file for complete search history.

(56) References Cited

U.S. PATENT DOCUMENTS 4,316,749 A * 2/1982 Evans et al. ................ 127/55

FOREIGN PATENT DOCUMENTS

EP 052541 A1 5/1982
WO 2012/047122 A1 4/2012

OTHER PUBLICATIONS

Wong et al: "Designing a lactose crystallization process based on dynamic metastable limit," Journal of Food Engineering vol. 111, Issue 4 (Mar. 1, 2012), pp. 642-654.

* cited by examiner

*Primary Examiner* — Layla Bland
(74) *Attorney, Agent, or Firm* — Dilworth & Barrese, LLP

(57) ABSTRACT

Suggested is a method for improving the yield during the production of crystalline alpha lactose, wherein
(a) an aqueous lactose solution is adjusted to a temperature of between about 62 and 67° C.,
(b) the solution is cooled down to between about 20 and 30° C.,
(c) the solution is held at this temperature for 0 to 5 h,
(d) subsequently, the solution is re-heated to between about 30 and 35° C.,
(e) the solution is held at this temperature for 0 to 5 h,
(f) then the solution is cooled down to about 10° C. and
(g) subsequently, the precipitated alpha lactose crystals are separated from the second mother liquor,
(h) an amount of a carbohydrate compound is added to the second mother liquor such that the solubility product of the residual amount of lactose that is still soluble is exceeded,
(i) the second amount of precipitated alpha lactose crystals is separated from the mother liquor, dried, and
(j) both amounts of alpha lactose crystals are combined.

15 Claims, 2 Drawing Sheets

Cooling curve according to the prior art

METHOD FOR INCREASING THE YIELD IN LACTOSE PRODUCTION (III)

FIELD OF THE INVENTION

The invention is in the field of dairy processing and relates to an improved method of lactose production.

PRIOR ART

Lactose belongs to the group of disaccharides and consists of the two molecules D-galactose and D-glucose, which are linked together by a β-1,4-glycosidic bond.

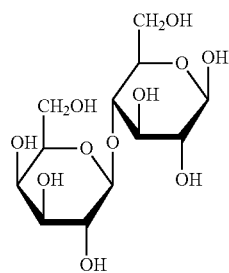

Lactose is a crystalline, colourless substance with a sweet taste; its sweetness is—depending on its concentration—between 25 and 60% that of the sweetness of saccharose. Lactose is a significant milk constituent and possesses a variety of nutriphysioiogical advantages. For example, it serves as a source of energy for the human metabolism, supports the resorption of calcium, hinders the development of putrefactive bacteria in the intestine and has a laxative effect when taken in larger doses. In food technology it is predominantly used for the production of lactic acid and as a texturizer for frozen foods. As it adds a creamy taste to foods, it is a widely used additive.

Lactose is a side product from the production of protein powders. In doing so, proteins are conventionally removed from whey by ultrafiltration and are subsequently subjected to spray-drying.

International patent application WO 2002 050089 A1 (Food Science Australia A) describes a method for the production of lactose which is commonly used today. In a first process step, the permeate obtained by ultrafiltration of the whey is concentrated by reverse osmosis (RO) or nanofiltration (NF). Subsequently, the concentrate thus obtained is demineralised in two steps, i.e., it is firstly reacted with an alkaline earth salt, usually an aqueous solution of calcium chloride, whereby the minerals are precipitated as calcium phosphate. During the second precipitation step the solubility of the calcium salts is further decreased by adding lower alcohols and another phosphate is precipitated. The separation of the salts is then carried out by means of suitable filtration devices such as, for example, membranes, separators or the like. The purified lactose solution is then subjected to vacuum distillation and adjusted to a solids content of about 65% by weight.

U.S. Pat. No. 4,202,909 also describes a method for obtaining lactose, wherein whey is firstly subjected to ultrafiltration, the resulting permeate is subjected to demineralisation, then the permeate is concentrated, followed by the separation of lactose from the mother liquor. In particular it describes that the mother liquor may be demineralised and processed again to obtain a further amount of lactose. GB 1575089 B is of a similar contents, with example 1describing a method for obtaining lactose, wherein in a first step whey is subjected to ultrafiltration, the UF permeate is subjected to demineralisation, the permeate is concentrated and lactose is then separated from the mother liquor.

It is conventional according to the methods of the prior art that the mother liquor, which contains about 90% by weight lactose in the dry matter, is introduced into the crystallisation tank following the condenser. Said tank is heated for the introduction process to keep the lactose in solution. Pure beta-lactose is present above a temperature of 93.5° C. During the cooling process it is quantitatively transformed to alpha lactose. However, this is not a clear-cut phase transition, because, firstly, a metastable phase is passed through, from which alpha lactose crystals separate. After further cooling, this is usually followed by the saturation curve allowing the crystals enough time for growth.

After the start of the crystallisation process the temperature is reduced to between 30 and 40° C., the liquor is—where required—allowed to sit for a period of 1 to 3 h at this temperature and is then further cooled down to 10° C. The complete cooling time is about 20 h It is problematic that said cooling process repeatedly involves phases of metastable condition, in which new crystal nuclei may again form, which, however, have little time for growth and thus remain very small. As the newly formed tiny crystals with a diameter of less than 80 μm are not collected during the separation of alpha lactose crystals, which is carried out in a decanter, about 17% of the lactose is lost.

In addition, stirring in the decanter causes crystals to break, in the process of which material is formed that cannot be separated due to its low particle diameter. Another 20% of the lactose is lost this way, eventually resulting in a lactose content of the mother liquor of between 35 and 40% which needs to be processed with a high effort such that an acceptable yield—considering the overall analysis of the process—may be obtained.

It is obvious that any improvement of the process that my lead to a reduction of the residual amount of lactose in the mother liquor would have a considerable impact on the economy of the process. It has thus been the object of the present, invention to improve existing methods of lactose production to this effect and to restrict the residual amount in alpha lactose to a maximum of 10% by weight, which is lost together with the mother liquor after crystallisation.

DESCRIPTION OF THE INVENTION

The subject matter of the invention is a method for improving the yield during the production of crystalline alpha lactose, wherein (a) an aqueous lactose solution is adjusted to a temperature of between about 62 and 67° C.,
(b) the solution is then cooled down to between about 20 and 30° C.,
(c) the solution is held at this temperature for a period of from 0 to 5 h,
(d) the solution is subsequently heated to between about 30 and 35° C.,
(e) the solution is held at this temperature for a period of from 0 to 5 h,
(f) the solution is then cooled down to about 10° C., and
(g) subsequently, the precipitated alpha lactose crystals are separated from the second mother liquor,
(h) an amount of a carbohydrate compound is added to the second mother liquor such that the solubility product of the residual amount of lactose that is still soluble is exceeded, (i) the second amount of precipitated alpha lactose crystals is separated from the mother liquor, dried, and (j) both amounts of alpha lactose crystals are combined.

Surprisingly it has been found that as a result of intermediate re-heating of the lactose solution small crystals and particles from crystal abrasion are solubilized again, thus being available for growing onto larger crystals. In this manner it is possible to divide about in half the loss in lactose due to the breaking of crystals and insufficient decanting; as a result, the remaining mother liquor after decanting only has a lactose content of a maximum of 20% by weight. By adding an amount of up to 5% by weight of a sugar, particularly, of glucose, the solubility product of lactose can be shifted such that only from about 5 to 10% by weight lactose remain in the mother liquor.

BRIEF DESCRIPTION OF THE DRAWINGS

The present invention will be described in greater detail with reference to the accompanying drawings in which.

DESCRIPTION OF THE PREFERRED EMBODIMENTS

Lactose Solutions

Figure 1:
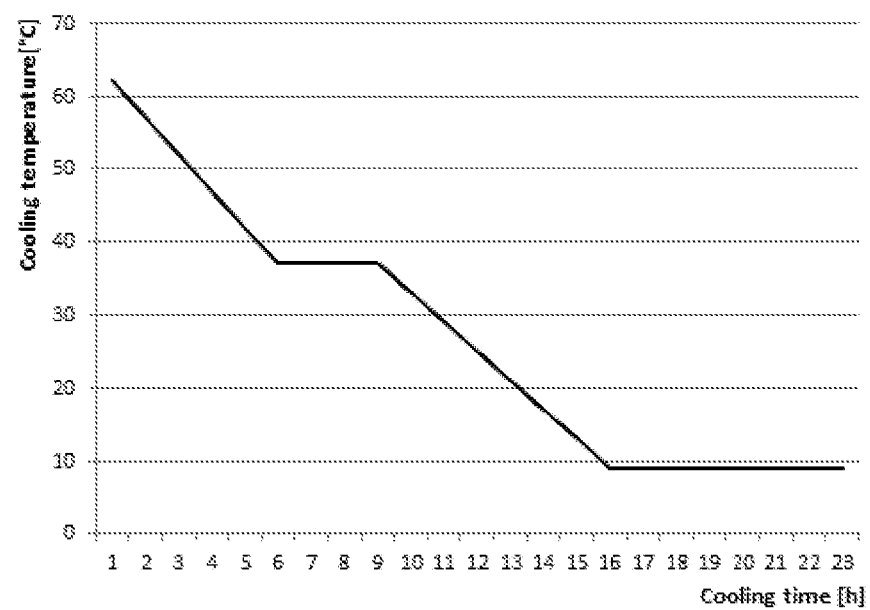
FIG. 1 is a graph of a time/temperature profile for production of crystalline alpha lactose according to the prior art.

Lactose solutions, which in the meaning of the method of the invention are suitable as starting materials for obtaining alpha lactose crystals, are usually obtained on the basis of whey. To this end, whey is firstly separated into a protein-rich and a lactose-rich fraction. The preferred separation in this case is ultrafiltration (UF), in which the UF retentate is further processed to obtain proteins, and the UF permeate is used to obtain lactose. Typically, the UF retentate contains a dry matter of about 20% by weight, of which about 2% by weight is lactose, while the ash content is about 1% by weight. In contrast, the UF permeate which is further processed to produce lactose has a content of dry matter of from about 4.5 to 5.5% by weight, wherein the lactose content is from about 4.1 to 4.6 and the ash content is from about 0.3 to 0.5.

An optional, but generally preferred step is concentrating the UF permeate by adjusting a dry matter content of from about 10 to 30% by weight—corresponding to 10 to 30° Brix—. This is preferably carried out by reverse osmosis (RO) or nanofiltration (NF).

The UF permeate shows—if applicable, after concentrating—a mineral content in the order of from 1 to 2% by weight. To allow the solutions to reach the specification which is at below 0.3% by weight, they are firstly adjusted to a near neutral pH value in the range of from 6 to 8 by adding bases, and an amount of a solution of a water-soluble calcium salt is added to the minerals, which essentially are soluble phosphates, such that slowly soluble calcium salts are precipitated. To adjust the pH value and to precipitate NaOH, an aqueous preparation of calcium chloride and alkali hydroxide or calcium hydroxide is used. In principle, alkaline or earth alkaline bases such as, for example, —KOH may be used to adjust the pH value. The nature of the precipitating salt is uncritical per se, for example, barium salts may precipitate. However, the use of calcium salts has the advantage that the precipitating agent has a reasonable cost and the salts have a very low solubility product, i.e. precipitation is essentially complete. Also without adding precipitating agents, demineralisation is carried out in stirrer vats, in the process of which it has proven to be advantageous to adjust a temperature in the range of from about 50 to 90 and, preferably, of about 80° C. Precipitation time is typically between about 20 and 120 and, preferably, between about 30 and 45 min, whereby said indications are to be understood to merely serve as reference purposes, as lower temperatures require longer reaction times and vice versa. After precipitation the salts are separated, for example, in separators that exploit the greater specific weight of the precipitated particles. However, it is also possible to perform separation, for example, by means of membrane filters during another ultrafiltration process within the range of 5 to 150 kDa, preferably, 10 to 50 kDa.

At this point, the purified flow typically contains from 15 to 20, preferably, about 17.5% by weight lactose while the ash content has already been reduced to about 0.8. If desired or required, a second demineralisation step may follow in which an amount of lower alcohols, particularly ethanol, is added to the pre-purified flow to further reduce the solubility product of the calcium salts still contained. In doing so, another amount of salts may be precipitated, if so required, and separated as described above.

In a second optional, but also generally preferred step the demineralised lactose-rich stream is concentrated again after leaving the filtering device, whereby a solids content Is adjusted which is essentially identical with the lactose content of about 50 to 70% by weight, corresponding to about 40 to 50° Brix. This is preferably performed fay vacuum evaporation in which the product is evaporated to, preferably, about 65% by weight and, optionally, also alcohol from the demineralisation step is separated. The aqueous lactose solutions thus obtained may be introduced in the crystallisation step.

Crystallisation Method

In the first step of the process, a lactose solution which is obtainable as described above and contains from about 60 to 95 and, preferably, from about 85 to 90% by weight lactose in dry matter, is pumped into a preheated crystallisation tank. This may be carried out continuously or batch-wise, depending on the devices used. The mother liquor may be adjusted to a temperature of above 93.5° C. before filling the tank to prevent the formation of alpha lactose; however, this is not compulsory. It is also possible to use mother liquors in which the transformation of beta into alpha lactose has already begun. Within the tank, the solution is cooled down to between 62 and 67 and, preferably, between about 63 and 65° C. To this end, it is sufficient to allow the hot lactose solution to adapt to the starting temperature of the crystallisation tank, which is usually the case within a period of between 1 and 2 h.

Subsequently, the lactose solution is continuously cooled down at a rate of about 1 to 5° K/h to a temperature of between about 20 and 30 and, preferably, between about 23 and 26° C. and held there for a period of about 0 to 5 and, preferably, of about 1 to 3 h. During said temperature curve meta-stabile phases are repeatedly passed through, in which—depending on the direction of the temperature—nuclei are formed or dissolved. As a result, however, new crystal nuclei are being formed, which during further cooling barely have a chance to reach a sufficient size such that they may be separated in the decanter. Therefore, the solution is again gently heated in the following step, particularly up to between about 30 and 45 and, preferably, between about 32 and 42° C. Again, the solution is held at this temperature for a period of about 0.5 to 5 and particularly from about 1 to 3 h. Again, in principle, heating may be performed as quickly as possible, for example, at a rate of from about 1 to 5° K/h.

As a result of these measures the crystal nuclei are solubilized again and may now grow onto larger crystals. To this end, the solution is now cooled down at a rate of from about 1 to 3° K/h to about 10° C., preferably, 5 to 10° C. and held at this temperature for a period of about 12 to 15 h thus allowing the alpha lactose crystals sufficient time to separate.

A total time for carrying out the cooling process may be scheduled to be from about 18 to 24 and, preferably, about 20 h. Subsequently, the lactose crystals are separated from the mother liquor which is preferably carried out by means of decanters working according to the centrifugal principle. In principle, also any other component that allows a solid/liquid separation is suitable for this step. This includes, for example, separators on the basis of membranes. The lactose crystals still having mother liquor attached are gently dried in the following, particularly by means of belt dryers which have proven to be particularly suitable.

Addition of Carbohydrates

Carbohydrates that are particularly suitable for significantly reducing the solubility product of lactose are, particularly, mono and/or disaccharides, including both aldoses and ketoses. Typical examples include

- trioses such as, for example D- and L-glyceraldehyde or dihydroxyacetone;
- tetroses such as, for example, D-erythrose or D-threose;
- pentoses such as, for example, D-ribose, D- and L-xylulose;
- hexoses such as, for example, D-glucose, D-mannose, D-gulose, D-idose, D-galactose, D-glucuronic acid, D-galacturonic acid, N-Acetyl-D-glucosamine, D-glucosamin, D-fructose, and L-rhamnose;
- Glucose-based disaccharides such as, for example, cellobiose, gentiobiose, isomaltose, isomaltulose, lactulose, laminaribiose, maltose, maltulose, melibiose, neohesperidose, neotrehalose, nigerose, rutinose, sophorose, saccharose and trehalose.

Besides D-glucose, glucose-rich carbohydrate fractions are particularly preferred, as they are easily accessible and cost-efficient and lead to an acceptable reduction of the solubility product at the same time. For cost reasons and because of their easy availability, sugar beet syrup or corn starch syrup are particularly preferred for use.

The carbohydrates may be added to the lactose mother liquors in amounts of up to 5% by weight. Preferably, the added amount is from about 0.1 to 3 and, particularly, from about 1 to 2% by weight Industrial Application Another subject matter of the present patent application relates to mother liquor with a content in alpha lactose of from about 15 to 20% by weight obtainable by the method of the invention.

The invention further comprises a method for the production of lactose, wherein (i) whey is subjected to a separation process in which a protein-rich and a lactose-rich fraction is obtained,
(ii) the lactose-rich fraction is (optionally after concentrating the main flow) subjected to demineralisation in which slowly soluble salts are precipitated,
(ii) the demineralised residue is cooled down, optionally after further concentration, until lactose precipitates in crystalline form,
(iii) the lactose crystals are separated from the mother liquor and dehydrated, characterized in that (a) the first mother liquor is adjusted to a temperature of between about 62 and 67° C.,
(b) the solution is then cooled down to a temperature of between about 20 and 30° C.,
(c) the solution is held at this temperature for a period of from 0 to 5 h,
(d) subsequently, the solution is re-heated to a temperature of between about 30 and 35° C.,
(e) the solution is held at this temperature for a period of from 0 to 5 h,
(f) then the solution is cooled down to about 10° C. and
(g) subsequently, the precipitated alpha lactose crystals are separated from the second mother liquor,
(h) an amount of a carbohydrate compound is added to the second mother liquor such that the solubility product of the residual amount of lactose that is still soluble is exceeded,
(i) the second amount of precipitated alpha lactose crystals is separated from the mother liquor, dried, and
(j) both amounts of alpha lactose crystals are combined.

EXAMPLES

Comparison Example V1

Lactose mother liquor with a content of 89.5% by weight in the dry matter and a temperature of about 70° C. was placed into a crystallisation tank which was preheated to 65° C., where it was cooled down to 65° C. at a rate of about 3° K/h within about 1 h and was held at this temperature for a period of no more than an hour before the solution was cooled down to 25° C. at a rate of about 3° K/h within about 1 h. The solution was held there at this temperature for a period of another 3 h and was then cooled down to 10° C. at a rate of 1° K/h within 1 h. With the onset of crystal separation, the solution was held at this temperature for a period of about 15 h, the precipitated alpha lactose crystals were separated in a decanter and any attached moisture was removed on a belt dryer. The remaining mother liquor had a residual content of 34.7% by weight lactose. FIG. 1 represents the temperature/time profile.

Example 1

Figure 2:
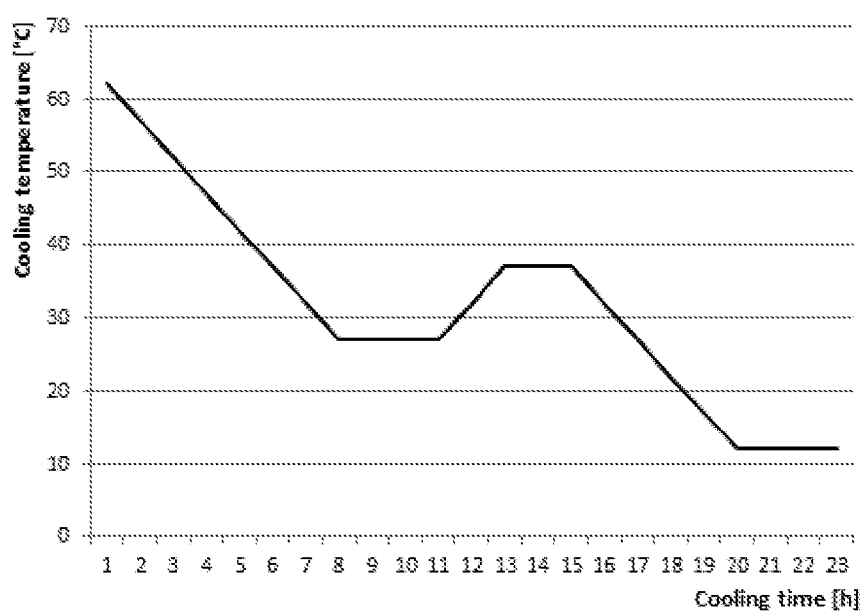
FIG. 2 is a graph of a time/temperature profile for production of crystalline alpha lactose according to the present invention.

The lactose mother liquor of comparison example V1 with a temperature of about 95° C. was placed into a crystallisation tank which was preheated to 65° C., where it was cooled down to 65° C. at a rate of about 3° K/h within about 1 h and was held there for a period of no more than an hour before the solution was cooled down to 25° C., again at a rate of about 3° K/h within about 1 h. The solution was held there at this temperature for a period of another 3 h and was then re-heated to 37° C. at a rate of about 3° K/h. The solution was held at this temperature for another period of 3 h and was then cooled down to 10° C. at a rate of 1° K/h within 1 h. With the onset of crystal separation, the solution was held at this temperature for a period of about 12 h, the precipitated alpha lactose crystals were separated in a decanter and any attached moisture was removed on a belt dryer. The remaining mother liquor had a residual content of 18.4% by weight lactose. FIG. 2 represents the temperature/time profile.

Comparison Example V2

Without the Addition of Carbohydrates

A first lactose mother liquor with a content of 89.5% by weight in the dry matter and a temperature of about 95° C. was placed into a crystallisation tank which was pre-heated to 65° C., where it was cooled down to 65° C. at a rate of about 3° K/h within about 1 h and was held at this temperature for a period of no more than an hour before the solution was cooled down to 25° C. at a rate of about 3° K/h within about 1 h. The solution was held there at this temperature for a period of another 3 h and was then cooled down to 10° C. at a rate of 1° K/h within 1 h. With the onset of crystal separation, the solution was held at this temperature for a period of about 15 h, the precipitated alpha lactose crystals were separated in a decanter and any attached moisture was removed on a belt dryer. The remaining second mother liquor had a residual content of 34.7% by weight lactose.

Examples 2 to 6

Addition of Between 0.1 and 5% by Weight Glucose

Between 0.1 and 5% by weight glucose were added to the mother liquor of example 1. The solution was homogenized and then cooled down again as described above, and the additional amount of lactose crystals obtained by reducing the solubility product was separated. Table 1 represents the residual content of lactose in the third mother liquor such obtained depending on the amount of glucose added.

TABLE 1

Residual content of lactose in the last mother liquor (% by weight)

| Example | Amount of glucose | Residual content of lactose in the mother liquor |
|---|---|---|
| Control | 0 | 18.4 |
| 2 | 0.1 | 9.7 |
| 3 | 0.5 | 8.8 |
| 4 | 1.0 | 7.6 |
| 5 | 2.0 | 5.2 |
| 6 | 5.0 | 5.2 |

Examples 7 to 11

Addition of 2% by Weight Carbohydrates

2% by weight of different carbohydrates were added to the mother liquor of example 1. The solution was homogenized and then cooled down again as described above, and the additional amount of lactose crystals obtained by reducing the solubility product was separated.

Table 2 represents the residual content of lactose in the third mother liquor such obtained depending on the amount of glucose added.

TABLE 2

Residual content of lactose in the last mother liquor (% by weight)

| Example | Carbohydrate | Residual content of lactose in the mother liquor |
|---|---|---|
| Control | None | 18.4 |
| 7 | Glucose | 5.2 |
| 8 | Saccharose | 5.8 |
| 9 | Molasses | 6.2 |
| 10 | Sugar beet syrup | 6.5 |
| 11 | Corn starch syrup | 6.7 |

The invention claimed is:

1. A method for improving the yield during the production of crystalline alpha lactose, wherein
   (a) an aqueous lactose solution is adjusted to a temperature of between about 62 and 67° C.,
   (b) the solution is then cooled down to between about 20 and 30° C.,
   (c) the solution is held at this temperature for a period of from 0 to 5 h,
   (d) the solution is subsequently heated to between about 30 and 45° C.,
   (e) the solution is held at this temperature for a period of from 0 to 5 h,
   (f) the solution is then cooled down to about 10° C., and
   (g) subsequently, the precipitated first amount of alpha lactose crystals is separated from the mother liquor,
   (h) an amount of a carbohydrate compound is added to the mother liquor such that the solubility product of the residual amount of lactose that is still soluble is exceeded,
   (i) the second amount of precipitated alpha lactose crystals is separated from the mother liquor, dried, and
   (j) both amounts of alpha lactose crystals are combined.

2. The method of claim 1, wherein the lactose solution under step (a) is adjusted to between 63° C. and 65° C.

3. The method of claim 1, wherein the solution under step (b) is cooled down at a rate of from about 1 to 5° K/h.

4. The method of claim 1, wherein the solution under step (b) is cooled down to between 23 and 26° C.

5. The method of claim 1, wherein the solution under step (c) is held at this temperature for a period of about 1 to 3 h.

6. The method of claim 1, wherein the solution under step (d) is heated to between about 32 and 42° C.

7. The method of claim 1, wherein the solution under step (d) is held at this temperature for a period of about 1 to 3 h.

8. The method of claim 1, wherein the solution under step (f) is cooled down at a rate of about 1 to 5° K/h.

9. The method of claim 1, wherein the temperature profile comprising steps (a) to (g) is passed through within a period of about 18 to 24 h.

10. The method of claim 1, wherein the alpha lactose crystals are separated by means of a decanter.

11. The method of claim 1, wherein mono- or disaccharides are used as carbohydrate compounds.

12. The method of claim 11, wherein mono- or disaccharides are used which are selected from the group consisting of trioses, tetroses, pentoses, hexoses and/or glucose-based disaccharides.

13. The method of claim 11, wherein glucose or a carbohydrate fraction that is rich in glucose is used.

14. The method of claim 1, wherein carbohydrate compounds are added to the mother liquor in amounts of up to 5% by weight.

15. A method for the production of crystalline alpha lactose, wherein
   (i) whey is subjected to a separation process in which a protein-rich and a lactose-rich fraction is obtained,
   (ii) the lactose-rich fraction is (optionally after concentrating the main flow) subjected to demineralisation in which slowly soluble salts are precipitated,
   (iii) the demineralised residue is cooled down, optionally after further concentration, until lactose precipitates in crystalline form,
   (iv) the lactose crystals are separated from the mother liquor and evaporated,
   wherein
   (a) the first mother liquor is adjusted to a temperature of between about 62 and 67° C.,
   (b) the solution is then cooled down to between about 20 and 30° C.,
   (c) the solution is held at this temperature for a period of from 0 to 5 h,
   (d) the solution is re-heated to between about 30 and 35° C., (e) the solution is held at this temperature for a period of from 0 to 5 h,
(f) then the solution is cooled to about 10° C. and
(g) subsequently, the precipitated alpha lactose crystals are separated from the second mother liquor,
(h) an amount of a carbohydrate compound is added to the second mother liquor such that the solubility product of the residual amount of lactose that is still soluble is exceeded,
(i) the second amount of precipitated alpha lactose crystals is separated from the mother liquor, dried, and
(j) both amounts of alpha lactose crystals are combined.

* * * * *